(12) United States Patent
Patel

(10) Patent No.: US 7,709,013 B2
(45) Date of Patent: May 4, 2010

(54) COMPOSITIONS HAVING IMPROVED SOFT FOCUS EFFECT PROPERTIES

(75) Inventor: Dhaval Patel, Edison, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 11/342,913

(22) Filed: Jan. 31, 2006

(65) Prior Publication Data

US 2007/0179241 A1     Aug. 2, 2007

(51) Int. Cl.
  *A61K 8/02*    (2006.01)
(52) U.S. Cl. .................. 424/401; 524/588; 524/443; 523/216; 523/210
(58) Field of Classification Search .............. 424/401; 524/443, 588; 523/216, 210
  See application file for complete search history.

(56) References Cited

U.S. PATENT DOCUMENTS

| | | | |
|---|---|---|---|
| 5,320,834 A | 6/1994 | Ounanian et al. | |
| 6,875,264 B2 * | 4/2005 | Zimmermann et al. | ...... 106/446 |
| 2003/0031692 A1 | 2/2003 | Jager Lezer | |
| 2003/0072780 A1 | 4/2003 | Ionita-Manzatu et al. | |
| 2003/0113357 A1 | 6/2003 | Bell et al. | |
| 2005/0025730 A1 | 2/2005 | Chevalier et al. | |
| 2005/0031658 A1 | 2/2005 | Girier Dufournier et al. | |
| 2005/0048016 A1 | 3/2005 | Lebreton et al. | |
| 2005/0074473 A1 | 4/2005 | Kosbach et al. | |
| 2005/0191329 A1 | 9/2005 | Taniguchi | |
| 2005/0220728 A1 | 10/2005 | Kanji et al. | |
| 2005/0265938 A1 * | 12/2005 | Cohen et al. | ................... 424/63 |

* cited by examiner

*Primary Examiner*—Margaret G Moore
(74) *Attorney, Agent, or Firm*—Oblon, Spivak, McClelland, Maier & Neustadt, L.L.P.

(57) ABSTRACT

The invention relates to a composition, especially a cosmetic composition, containing at least one silicone elastomer and at least one encapsulated pigment, wherein the refractive index of the pigment is greater than the refractive index of the encapsulating material.

24 Claims, No Drawings

COMPOSITIONS HAVING IMPROVED SOFT FOCUS EFFECT PROPERTIES

FIELD OF THE INVENTION

The present invention generally relates to compositions, for example, cosmetic make-up compositions, comprising at least one silicone elastomer and at least one encapsulated pigment, wherein the refractive index of the pigment is greater than the refractive index of the encapsulating material. Such compositions possess improved soft focus effect properties, particularly improved matity properties.

DISCUSSION OF THE BACKGROUND

Many cosmetic compositions have been developed for the purpose of attempting to hide skin defects or imperfections such as, for example, wrinkles, fine lines, pores, roughness, etc. Such attempts have included incorporating ingredients into the compositions which reflect and/or diffuse light to de-emphasize the defects and imperfections. Emmert, "Quantification of the Soft-Focus Effect," Cosmetics and Toiletries, 111, 57-61 (1996) discusses attempting to create a soft focus effect using such light-diffusing/scattering ingredients. When soft focus index is high, a composition produces a large soft focus effect, serving to mask defects by changing the perception of relief.

In the past, cosmetic compositions have employed ingredients such as silicone elastomers, planar powders, spherical powders such as silica, PMMA, barium sulfate, etc., and/or powders with a high refractive index such as titanium dioxide, zinc oxide and iron oxide in an attempt to achieve a soft-focus effect. However, such products have had drawbacks such as, for example, an unnatural look on skin owing to the use of highly opaque materials and the highlighting of skin defects owing to the use of planar materials. Moreover, such products have not generally had optimal or desirable soft focus effect properties. Thus, there remains a need for suitable cosmetic compositions having improved soft focus effect properties.

Accordingly, one aspect of the present invention is a care and/or makeup and/or treatment composition for keratinous material such as the skin and/or the lips which is able to provide improved soft focus effect properties upon application.

SUMMARY OF THE INVENTION

The present invention relates to compositions, preferably cosmetic compositions, comprising at least one silicone elastomer and at least one encapsulated pigment, wherein the refractive index of the pigment is greater than the refractive index of the encapsulating material.

The present invention also relates to compositions, preferably cosmetic compositions, comprising at least one silicone elastomer and at least one encapsulated pigment, wherein the refractive index of the pigment is greater than the refractive index of the encapsulating material and wherein the silicone elastomer(s) and the encapsulated pigment(s) provide synergistically improved soft focus effect properties to the compositions, particularly synergistically improved matity properties.

The present invention further relates to methods of increasing the soft-focus effect properties of a composition applied to a keratin material such as skin comprising combining at least one silicone elastomer and at least one encapsulated pigment, wherein the refractive index of the pigment is greater than the refractive index of the encapsulating material.

The present invention also relates to methods of increasing the matity properties of a composition applied to a keratin material such as skin comprising combining at least one silicone elastomer and at least one encapsulated pigment, wherein the refractive index of the pigment is greater than the refractive index of the encapsulating material.

The present invention further relates to methods of camouflaging and/or disguising skin imperfections comprising applying a skin imperfection camouflaging and/or disguising effective amount of a composition comprising at least one silicone elastomer and at least one encapsulated pigment, wherein the refractive index of the pigment is greater than the refractive index of the encapsulating material, to skin in need of such camouflaging or disguising.

The present invention also relates to methods of treating, caring for and/or making up keratinous material (for example, skin) by applying compositions of the present invention to the keratinous material in an amount sufficient to treat, care for and/or make up the keratinous material.

The present invention further relates to methods of enhancing the appearance of keratinous material (for example, skin) by applying compositions of the present invention to the keratinous material in an amount sufficient to enhance the appearance of the keratinous material.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

The cosmetic compositions and methods of the present invention can comprise, consist of, or consist essentially of the essential elements and limitations of the invention described herein, as well as any additional or optional ingredients, components, or limitations described herein or any otherwise useful ingredient found in personal care compositions intended for topical application to keratin materials.

The composition of the present invention may be in any form. For example, it may be a paste, a solid, a gel, or a cream or a powder. It may be an emulsion, such as an oil-in-water or water-in-oil emulsion, a multiple emulsion, such as an oil-in-water-in-oil emulsion or a water-in-oil-in-water emulsion, or a solid, rigid or supple gel, including anhydrous gels. The composition can also be in a form chosen from a translucent anhydrous gel and a transparent anhydrous gel. The composition of the invention may, for example, comprise an external or continuous fatty phase. The composition may be anhydrous. In another embodiment, the composition of the invention may be transparent or clear, including for example, a composition without pigments. The composition can also be a molded composition or cast as a stick or a dish. The composition in one embodiment is a solid such as a molded stick or a poured stick. The compositions of the present invention may also be in the form of a lip composition such as a lipstick or a liquid lip color, a foundation or a mascara product.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as phase separation if the composition is in the form of an emulsion, bending or leaning if the composition is in stick form, melting, or syneresis (or sweating). The stability is further tested by repeating the 8-week test at 4° C., 25° C., 37° C., 45° C., and/or under freeze-thaw conditions. A composition is considered to lack stability if in any of these tests an abnormality that impedes functioning of the composition is observed. The skilled artisan will readily recognize an abnormality that impedes functioning of a composition based on the intended application.

In accordance with the present invention, soft focus effect properties include at least three optical parameters: transparency, haze and matity.

Transparency relates to hemispherical transmittance (Th) or transmitted light. The greater the value of Th, the more transparent a composition is. Th can be measured using a spectrophotometer and an integration sphere placed behind a composition that is to be characterized. Exemplary methods for determining transparency are discussed in U.S. Ser. No. 10/902,894, filed Aug. 2, 2004 (published as U.S. patent application publication No. 2005/0031658) and U.S. Ser. No. 10/902,185, filed Jul. 30, 2004 (published as U.S. patent application publication No. 2005/0025730), the entire disclosures of both of which are hereby incorporated by reference.

Haze refers to magnitudes ((Th−Td/Th)×100) where Th represents hemispherical transmittance and Td represents a direct transmission factor. Th and Td can be measured using a spectrophotometer and an integration sphere placed behind a composition that is to be characterized. Exemplary methods for determining haze are discussed in U.S. Ser. No. 10/902,894, filed Aug. 2, 2004 (published as U.S. patent application publication No. 2005/0031658) and U.S. Ser. No. 10/902,185, filed Jul. 30, 2004 (published as U.S. patent application publication No. 2005/0025730), the entire disclosures of both of which are hereby incorporated by reference.

Matity relates to the relationship between diffused light and reflected light. Matity can generally be represented by the formula Matity (M)=reflected light (R)/diffused light (D). Thus, Matity is inversely proportional to the ratio of diffused light (D) to reflected light (R).

In determining quantitative values for Matity, it is generally advisable to standardize reflected and diffused light ratios. This is due to the fact that the maximum value for Matity (that is, R/D) is 0.45 owing to the nature of reflected and diffused light. Accordingly, it is generally advisable to standardize Matity values by assigning the R/D ratio value of 0.45 the Matity value of 100% and adjusting measured R/D ratio values in accordance with this standardization to obtain Matity values.

Silicone Elastomer

According to the present invention, compositions comprising at least one silicone elastomer are provided. Any suitable silicone elastomer can be used in accordance with the present invention. Suitable silicone elastomers include, for example, emulsifying silicone elastomers such as polyglycerolated and/or hydrophilic emulsifying silicone elastomers such as alkoxylated silicone elastomers, and non-emulsifying silicone elastomers. Such silicone elastomers can be spherical or non-spherical.

Polyglycerolated Silicone Elastomers

Suitable polyglycerolated silicone elastomers include, for example, crosslinked elastomeric organopolysiloxanes that may be obtained by a crosslinking addition reaction of diorganopolysiloxane containing at least one hydrogen atom linked to silicon and of polyglycerolated compounds containing ethylenically unsaturated groups, especially in the presence of a platinum catalyst.

Preferably, the crosslinked elastomeric organopolysiloxane is obtained by a crosslinking addition reaction (A) of diorganopolysiloxane containing at least two hydrogens each linked to a silicone, and (B) of glycerolated compounds containing at least two ethylenically unsaturated groups, especially in the presence (C) of a platinum catalyst.

In particular, the organopolysiloxane may be obtained by reaction of a polyglycerolated compound containing dimethylvinylsiloxy end groups and of methylhydrogenopolysiloxane containing trimethylsiloxy end groups, in the presence of a platinum catalyst.

Compound (A) is the base reagent for the formation of elastomeric organopolysiloxane and the crosslinking is performed by an addition reaction of compound (A) with compound (B) in the presence of the catalyst (C).

Compound (A) is in particular an organopolysiloxane containing at least 2 hydrogen atoms linked to different silicon atoms in each molecule.

Compound (A) may have any molecular structure, in particular a linear chain or branched chain structure or a cyclic structure.

Compound (A) may have a viscosity at 25° C. ranging from 1 to 50,000 centistokes, especially in order to have good miscibility with compound (B).

The organic groups linked to silicon atoms of the compound (A) may be alkyl groups containing from 1 to 18 carbon atoms, such as methyl, ethyl, propyl, butyl, octyl, decyl, dodecyl (or lauryl), myristyl, cetyl or stearyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group. The said organic group is preferably chosen from methyl, phenyl and lauryl groups.

Compound (A) may thus be chosen from methylhydrogenopolysiloxanes containing trimethylsiloxy end groups, dimethylsiloxane-methylhydrogenosiloxane copolymers containing trimethylsiloxy end groups, dimethylsiloxane-methylhydrogenosiloxane cyclic copolymers, or dimethylsiloxane-methylhydrogenosiloxane-laurylmethylsiloxane copolymers containing trimethylsiloxy end groups.

Compound (B) may be a polyglycerolated compound corresponding to formula (B') below:

$$C_mH_{2m-1}\text{—}O\text{-}[Gly]_n\text{-}C_mH_{2m-1} \quad\quad (B')$$

in which m is an integer ranging from 2 to 6, n is an integer ranging from 2 to 200, preferably ranging from 2 to 100, preferably ranging from 2 to 50, preferably ranging from 2 to 20, preferably ranging from 2 to 10 and preferably ranging from 2 to 5, and in particular equal to 3; Gly denotes:

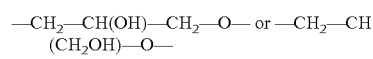

—CH$_2$—CH(OH)—CH$_2$—O— or —CH$_2$—CH(CH$_2$OH)—O—

Advantageously, the sum of the number of ethylenic groups per molecule of compound (B) and of the number of hydrogen atoms linked to silicon atoms per molecule of compound (A) is at least 4.

It is advantageous for compound (A) to be added in an amount such that the molar ratio between the total amount of hydrogen atoms linked to silicon atoms in compound (A) and the total amount of all the ethylenically unsaturated groups in compound (B) is within the range from 1/1 to 20/1.

Compound (C) is the crosslinking reaction catalyst, and is especially chloroplatinic acid, chloroplatinic acid-olefin complexes, chloroplatinic acid-alkenylsiloxane complexes, chloroplatinic acid-diketone complexes, platinum black and platinum on a support.

The catalyst (C) is preferably added in from 0.1 to 1,000 parts by weight, better still from 1 to 100 parts by weight, as clean platinum metal per 1,000 parts by weight of the total amount of compounds (A) and (B).

The polyglycerolated silicone elastomer may be conveyed in gel form in at least one hydrocarbon-based oil and/or one silicone oil.

Polyglycerolated silicone elastomers that may be used include, but are not limited to, those sold under the names "KSG-710", "KSG-810", "KSG-820", "KSG-830" and "KSG-840" by the company Shin-Etsu. Suitable polyglycerolated silicone elastomers are also disclosed in U.S. Ser. No. 11/085,509, filed Mar. 22, 2005 (published as U.S. patent application publication No. 2005/0220728), the entire disclosure of which is hereby incorporated by reference.

Hydrophilic Emulsifying Silicone Elastomers

The term "hydrophilic emulsifying silicone elastomer" means a silicone elastomer comprising at least one hydrophilic chain other than a polyglycerolated chain as described above.

In particular, the hydrophilic emulsifying silicone elastomer may be chosen from polyoxyalkylenated silicone elastomers.

Suitable polyoxyalkylenated silicone elastomers include crosslinked organopolysiloxanes that may be obtained by a crosslinking addition reaction of diorganopolysiloxane containing at least one hydrogen linked to silicon and of a polyoxyalkylene containing at least two ethylenically unsaturated groups.

Preferably, the polyoxyalkylenated crosslinked organopolysiloxane is obtained by a crosslinking addition reaction (A1) of diorganopolysiloxane containing at least two hydrogens each linked to a silicon, and (B1) of polyoxyalkylene containing at least two ethylenically unsaturated groups, especially in the presence (C1) of a platinum catalyst, as described, for example, in U.S. Pat. No. 5,236,986 and U.S. Pat. No. 5,412,004, the entire disclosures of which are hereby incorporated by reference.

The organopolysiloxane may be obtained by reaction of polyoxyalkylene (especially polyoxyethylene and/or polyoxypropylene) containing dimethylvinylsiloxy end groups and of methylhydrogenopolysiloxane containing trimethylsiloxy end groups, in the presence of a platinum catalyst.

The organic groups linked to silicon atoms of the compound (A1) may be alkyl groups containing from 1 to 18 carbon atoms, such as methyl, ethyl, propyl, butyl, octyl, decyl, dodecyl (or lauryl), myristyl, cetyl or stearyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

Compound (A1) may thus be chosen from methylhydrogenopolysiloxanes containing trimethylsiloxy end groups, dimethylsiloxane-methylhydrogenosiloxane copolymers containing trimethylsiloxy end groups, dimethylsiloxane-methylhydrogenosiloxane cyclic copolymers, dimethylsiloxane-methylhydrogenosiloxane-laurylmethylsiloxane copolymers containing trimethylsiloxy end groups.

Compound (C1) is the crosslinking reaction catalyst, and is especially chloroplatinic acid, chloroplatinic acid-olefin complexes, chloroplatinic acid-alkenylsiloxane complexes, chloroplatinic acid-diketone complexes, platinum black and platinum on a support.

Preferably, the polyoxyalkylenated silicone elastomers may be formed from divinyl compounds, in particular polyoxyalkylenes containing at least two vinyl groups, reacting with Si—H bonds of a polysiloxane.

The polyoxyalkylenated silicone elastomers may be conveyed in the form of a gel consisting of an elastomeric organopolysiloxane included in at least one hydrocarbon-based oil and/or one silicone oil.

Suitable polyoxyalkylenated elastomers are described in U.S. Pat. No. 5,236,986, U.S. Pat. No. 5,412,004, U.S. Pat. No. 5,837,793 and U.S. Pat. No. 5,811,487, the entire contents of which are incorporated herein by reference.

Suitable polyoxyalkylenated silicone elastomers that may be used include those sold under the names "KSG-21", "KSG-20", "KSG-30", "KSG-31", "KSG-32", "KSG-33", "KSG-210", "KSG-310", "KSG-320", "KSG-330", "KSG-340" and "X-226146" by the company Shin-Etsu, or "DC9010" and "DC9011" by the company Dow Corning.

Suitable hydrophilic emulsifying silicone elastomers are also disclosed in U.S. Ser. No. 11/085,509, filed Mar. 22, 2005 (published as U.S. patent application publication No. 2005/0220728), the entire disclosure of which is hereby incorporated by reference.

Non-Emulsifying Silicone Elastomers

The term "non-emulsifying" defines elastomers not containing a hydrophilic chain, such as polyoxyalkylene or polyglycerolated units.

The non-emulsifying silicone elastomer is preferably an elastomeric crosslinked organopolysiloxane that may be obtained by a crosslinking addition reaction of diorganopolysiloxane containing at least one hydrogen linked to silicon and of diorganopolysiloxane containing ethylenically unsaturated groups linked to silicon, especially in the presence of a platinum catalyst; or by dehydrogenation crosslinking coupling reaction between a diorganopolysiloxane containing hydroxyl end groups and a diorganopolysiloxane containing at least one hydrogen linked to silicon, especially in the presence of an organotin compound; or by a crosslinking coupling reaction of a diorganopolysiloxane containing hydroxyl end groups and of a hydrolysable organopolysilane; or by thermal crosslinking of organopolysiloxane, especially in the presence of an organoperoxide catalyst; or by crosslinking of organopolysiloxane via high-energy radiation such as gamma rays, ultraviolet rays or an electron beam.

Preferably, the elastomeric crosslinked organopolysiloxane is obtained by a crosslinking addition reaction (A2) of diorganopolysiloxane containing at least two hydrogens each linked to a silicon, and (B2) of diorganopolysiloxane containing at least two ethylenically unsaturated groups linked to silicon, especially in the presence (C2) of a platinum catalyst, as described, for example, in patent application EP0295886A, the entire disclosure of which is hereby incorporated by reference.

The organopolysiloxane may be obtained by reaction of dimethylpolysiloxane containing dimethylvinylsiloxy end groups and of methylhydrogenopolysiloxane containing trimethylsiloxy end groups, in the presence of a platinum catalyst.

Compound (A2) is the base reagent for the formation of elastomeric organopolysiloxane, and the crosslinking is performed by an addition reaction of compound (A2) with compound (B2) in the presence of a catalyst (C2).

Compound (A2) is advantageously a diorganopolysiloxane containing at least two lower (for example C2-C4) alkenyl groups; the lower alkenyl group may be chosen from vinyl, allyl and propenyl groups. These lower alkenyl groups may be located in any position on the organopolysiloxane molecule, but are preferably located at the ends of the organopolysiloxane molecule. The organopolysiloxane (A2) may have a branched-chain, linear-chain, cyclic or network structure, but the linear-chain structure is preferred. Compound (A2) may have a viscosity ranging from the liquid state to the gum state. Preferably, compound (A2) has a viscosity of at least 100 centistokes at 25° C.

The organopolysiloxanes (A2) may be chosen from methylvinylsiloxanes, methylvinylsiloxane-dimethylsiloxane copolymers, dimethylpolysiloxanes containing dimethylvinylsiloxy end groups, dimethylsiloxane-methylphenylsiloxane copolymers containing dimethylvinylsiloxy end groups, dimethylsiloxane-diphenylsiloxane-methylvinylsiloxane copolymers containing dimethylvinylsiloxy end groups, dimethylsiloxane-methylvinylsiloxane copolymers containing trimethylsiloxy end groups, dimethylsiloxane-methylphenylsiloxane-methylvinylsiloxane copolymers containing trimethylsiloxy end groups, methyl(3,3,3-trifluoropropyl)polysiloxanes containing dimethylvinylsiloxy end groups, and dimethylsiloxane-methyl(3,3,3-trifluoropropyl)siloxane copolymers containing dimethylvinylsiloxy end groups.

Compound (B2) is in particular an organopolysiloxane containing at least 2 hydrogens linked to silicon in each molecule and is thus the crosslinking agent for the compound (A2).

Preferably, the sum of the number of ethylenic groups per molecule of compound (A2) and the number of hydrogen atoms linked to silicon per molecule of compound (B2) is at least 4.

Compound (B2) may be in any molecular structure, especially of linear-chain or branched-chain structure, or cyclic structure.

Compound (B2) may have a viscosity at 25° C. ranging from 1 to 50,000 centistokes, especially in order to have good miscibility with compound (A).

It is advantageous for compound (B2) to be added in an amount such that the molar ratio between the total amount of hydrogen atoms linked to silicon in compound (B2) and the total amount of all of the ethylenically unsaturated groups in compound (A2) is within the range from 1/1 to 20/1.

Compound (B2) may be chosen from methylhydrogenopolysiloxanes containing trimethylsiloxy end groups, dimethylsiloxane-methylhydrogenosiloxane copolymers containing trimethylsiloxy end groups, and dimethylsiloxane-methylhydrogenosiloxane cyclic copolymers.

Compound (C2) is the crosslinking reaction catalyst, and is especially chloroplatinic acid, chloroplatinic acid-olefin complexes, chloroplatinic acid-alkenylsiloxane complexes, chloroplatinic acid-diketone complexes, platinum black and platinum on a support.

The catalyst (C2) is preferably added in from 0.1 to 1,000 parts by weight, better still from 1 to 100 parts by weight, as clean platinum metal per 1,000 parts by weight of the total amount of compounds (A2) and (B2).

Other organic groups may be linked to silicon in the organopolysiloxanes (A2) and (B2) described above, for instance alkyl groups such as methyl, ethyl, propyl, butyl or octyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

The elastomeric crosslinked organopolysiloxanes may be conveyed in the form of a gel consisting of an elastomeric organopolysiloxane included in at least one hydrocarbon-based oil and/or one silicone oil. The elastomeric crosslinked organopolysiloxanes may also be in powder form.

Suitable non-emulsifying silicone elastomers are described in patent applications JP61-194009 A, EP0242219 A, EP0295886 A and EP0765656 A, the entire contents of which are herein incorporated by reference.

Suitable non-emulsifying silicone elastomers that may be used include, but are not limited to, those sold under the names "DC 9040", "DC 9041", "DC 9509", "DC 9505" and "DC 9506" by the company Dow Corning.

Suitable non-emulsifying silicone elastomers are also disclosed in U.S. Ser. No. 11/085,509, filed Mar. 22, 2005 (published as U.S. patent application publication No. 2005/0220728), the entire disclosure of which is hereby incorporated by reference.

The non-emulsifying silicone elastomer may also be in the form of elastomeric crosslinked organopolysiloxane powder coated with silicone resin, especially with silsesquioxane resin, as described, for example, in U.S. Pat. No. 5,538,793, the entire content of which is herein incorporated by reference. Such elastomers are sold under the names "KSP-100", "KSP-101", "KSP-102", "KSP-103", "KSP-104" and "KSP-105" by the company Shin-Etsu.

Other elastomeric crosslinked organopolysiloxanes in the form of powders include hybrid silicone powders functionalized with fluoroalkyl groups, sold especially under the name "KSP-200" by the company Shin-Etsu; hybrid silicone powders functionalized with phenyl groups, sold especially under the name "KSP-300" by the company Shin-Etsu.

The silicone elastomer may be present in the compositions of the present invention in an amount of from 0.1% to 95% by weight, preferably from 0.1% to 75% by weight, more preferably from 0.1 to 50% by weight, more preferably from 0.1% to 40% by weight, more preferably from 0.5% to 30% by weight, more preferably from 0.5% to 25% by weight, more preferably from 1% to 20%, more preferably from 1% to 15% and even more preferably from 3% to 10% by weight based on the weight of the composition.

Encapsulated Pigments

According to the present invention, compositions comprising at least one encapsulated pigment are provided. Any suitable encapsulated pigment can be used in accordance with the present invention as long as the refractive index of the pigment is greater than the refractive index of the encapsulating material. Such encapsulated pigments can be spherical or non-spherical (for example, planar). In preferred embodiments, the encapsulated pigment is spherical.

In accordance with preferred embodiments, the encapsulating material may be any suitable material within which pigment may be encapsulated and which has a refractive index. Suitable encapsulating materials include, but are not limited to, silica, alumina and PMMA.

Also in accordance with preferred embodiments, the pigment to be encapsulated may be any suitable pigment which has a refractive index greater than the refractive index of the encapsulating material. For example, oxides such as titanium dioxide, zinc oxide and iron oxide are all suitable pigment materials for encapsulation in accordance with the present invention.

Examples of suitable encapsulated pigment materials include, but are not limited to, those encapsulated pigment products sold by Sunjin Chemical Co. Ltd. such as, for example, SUNSIL-Tin50, SUNSIL-TZin50, SUNSIL-TZin40, SUNSIL-Tin30 and SUNSIL-Tin40, as well as those encapsulated pigment products sold by Miyoshi such as, for example, those sold under the PC BALL label (for example, PC BALL PC-LL-100 P—silica microspheres containing yellow iron oxide)

The encapsulated pigment may be present in the compositions of the present invention in an amount of from 0.1% to 50% by weight, more preferably from 0.1% to 40% by weight, more preferably from 0.5% to 30% by weight, more preferably from 0.5% to 25% by weight, more preferably from 1% to 25%, more preferably from 3% to 25% and even more preferably from 5% to 25% by weight based on the weight of the composition.

Additional Additives

The composition of the invention can also comprise any additive usually used in the field under consideration. For example, non-encapsulated pigments, film forming agents, structuring polymers, dispersants, antioxidants, essential oils, preserving agents, fragrances, waxes, liposoluble polymers that are dispersible in the medium, fillers, neutralizing agents, cosmetic and dermatological active agents such as, for example, emollients, moisturizers, vitamins, anti-wrinkle agents, essential fatty acids, sunscreens, and mixtures thereof can be added. A non-exhaustive listing of such ingredients can be found in U.S. patent application Ser. No. 10/733,467, filed Dec. 12, 2003, the entire contents of which is hereby incorporated by reference. Further examples of suitable additional components can be found in the other references which have been incorporated by reference in this application, including but not limited to the applications from which this application claims priority. Still further examples of such additional ingredients may be found in the *International Cosmetic Ingredient Dictionary and Handbook* ($9^{th}$ ed. 2002).

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present).

According to preferred embodiments, the compositions comprise at least one non-encapsulated coloring agent chosen from pigments, dyes, such as liposoluble dyes, nacreous pigments, and pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, such as from 0.0001% to 6%.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, be present in the composition in a concentration ranging up to 50% by weight of the total weight of the composition, such as from 0.1% to 20%, preferably from 0.1% to 15%.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present, the non-encapsulated pigments may be present in the composition in a concentration ranging up to 50% by weight of the total weight of the composition, such as from 0.5% to 40%, and further such as from 2% to 30%. In the case of certain products, the pigments, including nacreous pigments, may, for example, represent up to 50% by weight of the composition.

In one embodiment, the composition of the present invention may contain sunscreens. Sunscreens may be inorganic nanoparticles or organic compounds. Sunscreens according to this embodiment may also include chemical absorbers which absorb harmful ultraviolet radiation. Specific examples of sunscreens that can be used are described in pages 2954-2955 of the *International Cosmetic Ingredient Dictionary and Handbook* ($9^{th}$ ed. 2002).

The sunscreens are generally present in the compositions according to the invention in proportions ranging from 0.1 to 30% by weight with respect to the total weight of the composition and preferably ranging from 0.2 to 15% by weight with respect to the total weight of the composition. When sunscreens are present in the invention composition, they are preferably present in an amount sufficient to provide the composition with an SPF value of at least 10 or above, including 15, 20, 25, 30, 35, 40, 45, 50, etc.

According to preferred embodiments of the present invention, the compositions are anhydrous. By "anhydrous," it is meant that the composition contains substantially no water (that is, less than about 0.1% by weight of the composition of water).

According to other preferred embodiments, the compositions of the present invention further comprise water. In this embodiment, water is preferably present in an amount ranging from about 0.1 to about 70%, preferably from about 0.5 to 55%, and more preferably from about 1 to about 45% relative to the total weight of the composition. Preferably, such water-containing cosmetic compositions are lip compositions (for example, lipstick or liquid lip colors), foundations or mascaras, and are emulsions or dispersions.

The composition according to the invention can be in the form of a tinted or non tinted dermatological composition or a care composition for keratin materials such as the skin, the lips and/or superficial body growths, in the form of an antisun composition or make-up-removing product in stick form. It can be used in particular as a care base for the skin, superficial body growths or the lips (lip balms, for protecting the lips against cold and/or sunlight and/or the wind, or care cream for the skin, the nails or the hair). As defined herein, a deodorant product is personal hygiene product and does not relate to care, make-up or treatment of keratin materials, including keratinous fibers.

The composition of the invention may also be in the form of a colored make-up product for the skin, in particular a foundation, optionally having care or treating properties, a blusher, a face powder, an eye shadow, a concealer product, an eyeliner, a make-up product for the body; a make-up product for the lips such as a lipstick, optionally having care or treating properties; a make-up product for superficial body growths such as the nails or the eyelashes, in particular in the form of a mascara cake, or for the eyebrows and the hair, in particular in the form of a pencil.

Needless to say, the composition of the invention should be cosmetically or dermatologically acceptable, i.e., it should contain a non-toxic physiologically acceptable medium and should be able to be applied to the skin, superficial body growths or the lips of human beings. For the purposes of the invention, the expression "cosmetically acceptable" means a composition of pleasant appearance, odor, feel and/or taste.

According to preferred embodiments of the present invention, methods of treating, caring for and/or making up keratinous material such as skin, lips, hair and mucous membranes by applying compositions of the present invention to the keratinous material in an amount sufficient to treat, care for and/or make up the keratinous material are provided.

According to other preferred embodiments, methods of covering or hiding defects associated with keratinous material such as imperfections or discolorations by applying compositions of the present invention to the keratinous material in an amount sufficient to cover or hide such defects are provided.

According to yet other preferred embodiments, methods of enhancing the appearance of keratinous material by applying compositions of the present invention to the keratinous material in an amount sufficient to enhance the appearance of the keratinous material are provided.

In accordance with the three preceding preferred embodiments, the compositions of the present invention are applied topically to the desired area of the skin in an amount sufficient to treat, care for and/or make up the keratinous material, to cover or hide defects associated with keratinous material, skin imperfections or discolorations, or to enhance the appearance of keratinous material. The compositions may be applied to the desired area as needed, preferably once or twice daily, more preferably once daily and then preferably allowed to dry before subjecting to contact such as with clothing or other objects. The composition is preferably applied to the desired area that is dry or has been dried prior to application.

According to preferred embodiments of the present invention, methods of increasing the soft-focus effect properties of a composition applied to a keratin material such as skin comprising combining at least one silicone elastomer and at least one encapsulated pigment, wherein the refractive index of the pigment is greater than the refractive index of the encapsulating material, are provided. Preferably, the silicone elastomer and the encapsulated pigment synergistically increase at least one soft-focus effect property.

According to other preferred embodiments, methods of increasing the matity properties of a composition applied to a keratin material such as skin comprising combining at least one silicone elastomer and at least one encapsulated pigment, wherein the refractive index of the pigment is greater than the refractive index of the encapsulating material, are provided. Preferably, the silicone elastomer and the encapsulated pigment synergistically increase matity.

The present invention also envisages kits and/or prepackaged materials suitable for consumer use containing one or more compositions according to the description herein. The packaging and application device for any subject of the invention may be chosen and manufactured by persons skilled in the art on the basis of their general knowledge, and adapted according to the nature of the composition to be packaged. Indeed, the type of device to be used can be in particular linked to the consistency of the composition, in particular to its viscosity; it can also depend on the nature of the constituents present in the composition, such as the presence of volatile compounds.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

Example 1

Foundation Primer

| Seq | Trade Name | CTFA Name | Amount |
|---|---|---|---|
| A | Water | Water | 40.90 |
|  | Glycerin | Glycerin | 5.00 |
|  | Hostacerin AMPS | Ammonium Polyacryloyldimethyl Taurate | 0.30 |
|  | Sepigel | Polyacrylamide (and) C13–14 Isoparaffin (and) Laureth-7 | 1.00 |
|  | KF-6100 | Polyglyceryl-3 Disiloxane Dimethicone | 2.00 |
| B | Phenonip | Phenonip | 0.80 |
|  | DC 245 Fluid | Cyclopentasiloxane | 15.00 |
|  | DC 9041 | Dimethicone (and) Dimethicone Crosspolymer | 30.00 |
| C | Sunsil Tin 50 | Silica (and) Titanium Dioxide | 5.00 |
|  |  | TOTAL | 100.00 |

Example 2

Foundation Primer

| Seq | Trade Name | CTFA Name | Amount |
|---|---|---|---|
| A | DC245 | Cyclopentasiloxane | 25.00 |
|  | Triethylhexanoin | Triethylhexanoin | 5.00 |
|  | DC 9041 | Dimethicone (and) Dimethicone Crosspolymer | 33.00 |
|  | Sunsil Tin50 | Silica + TiO2 | 7.50 |
|  | KSP 100 | Vinyl Dimethicone/Methicone Silsesquioxane Crosspolymer | 3.00 |
|  | KF-6017 | PEG-10 Dimethicone | 1.50 |
| B | Water | Water | 13.20 |
|  | Sodium Chloride | Sodium Chloride | 1.00 |
|  | Phenonip | Preservative | 0.80 |
|  | Glycerin | Glycerin | 10.00 |
|  |  | TOTAL | 100.00 |

Example 3

Comparative Example

The foundation primer of Example 1 containing both a silicone elastomer and an encapsulated pigment, wherein the refractive index of the pigment is greater than the refractive index of the encapsulating material, was compared to Comparative Examples 1 and 2. Comparative Examples 1 and 2 were essentially the same as Example 1 except that Comparative Example 1 did not contain any encapsulated pigment, and Comparative Example 2 did not contain any silicone elastomer. The properties of these three compositions were determined in accordance with the procedures discussed above and are reported in the following Table.

|  | Composition | | | |
| --- | --- | --- | --- | --- |
|  | Th | Td | Haze | Matity |
| Example 1 | 87 | 69 | 79.31 | 68 |
| Comparative Example 1 | 100 | 60 | 60 | 30 |
| Comparative Example 2 | 85 | 45 | 53 | 21 |

Example 1 possessed better haze than either Comparative Example 1 or Comparative Example 2. Also, Example 1 possessed synergistically better matity than Comparative Example 1 or Comparative Example 2. Thus, Example 1 possessed significantly improved soft focus effect properties over compositions which contained either a silicone elastomer or an encapsulated pigment.

What is claimed is:

1. A composition comprising at least one silicone elastomer and at least one encapsulated pigment, wherein the refractive index of the pigment is greater than the refractive index of the encapsulating material, and wherein the silicone elastomer(s) and the encapsulated pigment(s) synergistically improve matity of the composition.

2. The composition according to claim 1, wherein the silicone elastomer is spherical.

3. The composition according to claim 1, wherein the silicone elastomer is non-spherical.

4. The composition according to claim 1, wherein the silicone elastomer is non-emulsifying.

5. The composition according to claim 1, wherein the pigment is titanium dioxide.

6. The composition according to claim 1, wherein the pigment is zinc oxide.

7. The composition according to claim 1, wherein the encapsulating material is silica.

8. The composition according to claim 1, further comprising an active agent selected from the group consisting of sunscreen agents, moisturizing agents, anti-wrinkle agents, and mixtures thereof.

9. A method of making up skin or lips comprising applying the composition according to claim 1 to skin or lips.

10. The composition according to claim 1, wherein the pigment is titanium dioxide and the encapsulating material is silica.

11. A method of increasing the matity of a composition applied to skin comprising combining at least one silicone elastomer and at least one encapsulated pigment, wherein the refractive index of the pigment is greater than the refractive index of the encapsulating material.

12. The method according to claim 11, wherein the silicone elastomer is spherical.

13. The method according to claim 11, wherein the silicone elastomer is non-spherical.

14. The method according to claim 11, wherein the silicone elastomer is non-emulsifying.

15. The method according to claim 11, wherein the pigment is titanium dioxide.

16. The method according to claim 11, wherein the pigment is zinc oxide.

17. The method according to claim 11, wherein the encapsulating material is silica.

18. A method of increasing the soft-focus effect of a composition applied to skin comprising combining at least one silicone elastomer and at least one encapsulated pigment, wherein the refractive index of the pigment is greater than the refractive index of the encapsulating material.

19. The method according to claim 18, wherein the silicone elastomer is spherical.

20. The method according to claim 18, wherein the silicone elastomer is non-spherical.

21. The method according to claim 18, wherein the silicone elastomer is non-emulsifying.

22. The method according to claim 18, wherein the pigment is titanium dioxide.

23. The method according to claim 18, wherein the pigment is zinc oxide.

24. The method according to claim 18, wherein the encapsulating material is silica.

* * * * *